United States Patent [19]

Panchison

[11] Patent Number: 5,307,594

[45] Date of Patent: May 3, 1994

[54] METHOD FOR FORMING TEXTURED SURFACES ON AN ORTHOPAEDIC IMPLANT

[75] Inventor: Clarence M. Panchison, Warsaw, Ind.

[73] Assignee: Zimmer, Inc., Warsaw, Ind.

[21] Appl. No.: 990,320

[22] Filed: Dec. 14, 1992

[51] Int. Cl.$^5$ .............................................. B24C 1/04
[52] U.S. Cl. ...................................... 51/310; 51/312; 51/319
[58] Field of Search ................ 51/310, 312, 311, 319, 51/320, 321, 262 R, 419, 420, 421; 623/901

[56] References Cited

U.S. PATENT DOCUMENTS

| | | | |
|---|---|---|---|
| 3,328,925 | 7/1967 | Hewitt | 51/420 |
| 4,470,226 | 9/1984 | Williams | 511/310 |
| 4,612,737 | 9/1986 | Adee et al. | 51/310 |
| 4,801,490 | 1/1989 | Schuette | 51/311 |
| 4,865,603 | 9/1989 | Noiles | 623/18 |
| 5,057,108 | 10/1991 | Shetty et al. | 606/53 |

Primary Examiner—Jack Lavinder
Attorney, Agent, or Firm—Todd A. Dawson

[57] ABSTRACT

The method of this invention eliminates the problems discussed above. First a resilient mask 12 is placed on the implant 10. The mask 12 includes openings 14 which form the design of the textured surface. Next the implant 10 with mask 12 attached is subjected to high pressure blasting with a erosive blasting media. Typically, this may be referred to as media blasting. Particles contacting the resilient mask 12 are bounced off or embedded in the masking material while protecting the implant. Particles passing through the openings 14 of the mask 12 contact the surface of the implant 10. Blasting is continued until a proper surface is achieved. After blasting, the mask 12 is removed. Portions of the implant 10 which were exposed are blasted away or textured, portions protected by the mask 12 are unaffected.

2 Claims, 2 Drawing Sheets

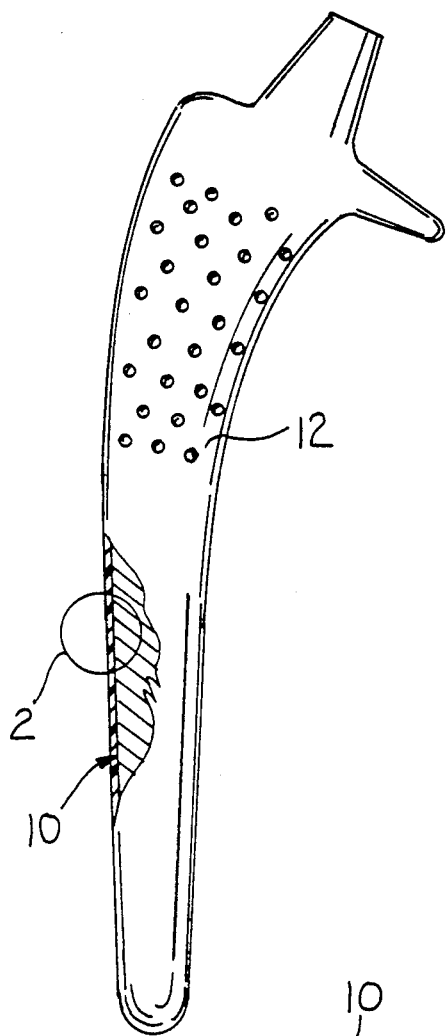
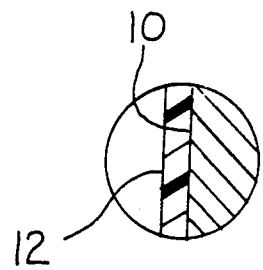
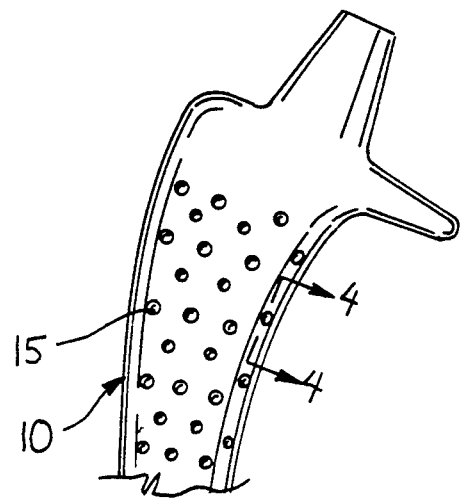
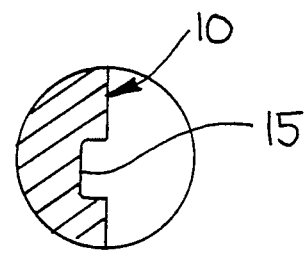

METHOD FOR FORMING TEXTURED SURFACES ON AN ORTHOPAEDIC IMPLANT

FIELD OF THE INVENTION

This invention relates to the field of textured orthopaedic implants and has specific relevance to a method of providing a surface texture on an orthopaedic implant.

BACKGROUND OF THE INVENTION

In the field of orthopaedics, it is considered advantageous to provide a textured surface on the outer portion of an orthopaedic implant to be placed within the prepared canal of a patient's bone. Such textured surfaces may be used to promote bone ingrowth or to enhance the mechanical bond between the implant and the bone cement used to hold the implant within the canal. Typically, these textured surfaces are formed by impacting a tool against the implant or by machining. A problem with the prior methods of forming textured surfaces is that it is generally cost prohibitive to place the textures on an implant surface. This problem results from the shape of the implant, cost of tooling to hold the implant, and generally makes the process impractical.

SUMMARY OF THE INVENTION

The method of this invention solves the problems discussed above. First a resilient mask is placed on the implant. The mask includes openings which form the design of the textured surface. Next the implant with mask attached is subjected to high pressure blasting with an erosive blasting media. This process may be referred to as media blasting. Particles contacting the resilient mask are bounced off. Particles passing through the opening of the mask contact the surface of the implant. Eventually, the particles will erode away the exposed outer surface of the implant. Blasting is continued until a proper surface depth is achieved. After blasting, the mask is removed. Portions of the implant which were exposed are textured, portions protected by the mask are unaffected.

By using the method of the invention, any design of textured surfaces may be placed at any location on the implant, curved or flat surfaces may be treated at the same time without the need for costly tooling.

Accordingly, it is an advantage of the invention to provide a novel method of forming a textured surface on a prosthetic implant.

Another advantage of the invention is to provide a low cost method of forming a textured surface on a hip stem implant.

Still other advantages of the invention will become apparent upon reading of the following description taken with the accompanying drawings.

BRIEF DESCRIPTION OF THE DRAWINGS

FIG. 1 is a elevational view of a hip stem covered with a mask suitable for performing the method of the invention with portions cut away and sectioned for illustrative purposes.

FIG. 2 is an enlarged view of the area circled in FIG. 1 designated by numeral 2.

FIG. 3 is an partial elevational view of the hip stem of FIG. 2 after blasting and with the mask removed to illustrate the textured surface formed by the method of the invention.

FIG. 4 is a sectional view taken along line 4—4 of FIG. 3.

DESCRIPTION OF THE PREFERRED EMBODIMENT

Figure 5:
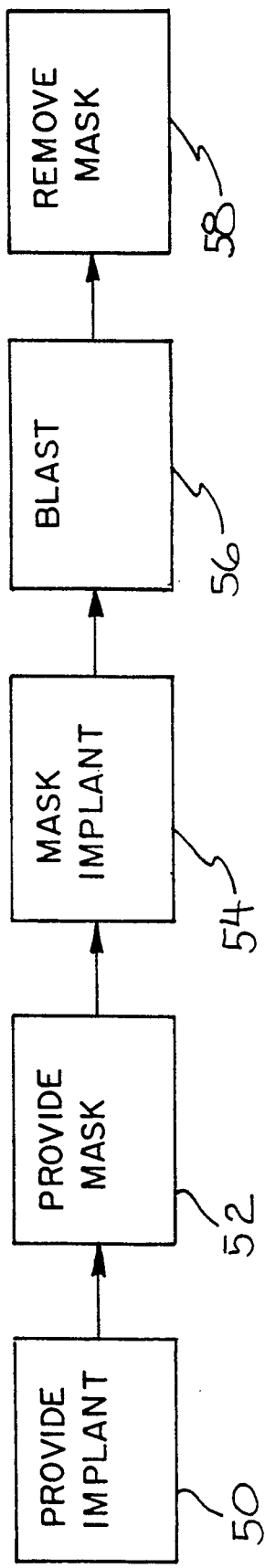
FIG. 5 is a block diagram illustrating the steps involved in the method of the invention.

The preferred embodiment herein described is not intended to be exhaustive or to limit the invention to the precise form disclosed. Rather, it is chosen and described to best explain the invention so that others skilled in the art might utilize its teachings.

Referring now to FIG. 5, the steps for texturing the surface of an orthopaedic implant device in accord with an exemplary embodiment of the present invention are diagrammatically illustrated. Generally, block 50 represents the first step of providing an orthopaedic implant device or a component part thereof, i.e., a metal substrate. Block 52 represents providing a mask having a predetermined designed formed therein. Block 54 represents placing the mask on the implant. Block 56 represents subjecting the implant and mask to media blasting for a predetermined period of time. Block 58 represents removing the mask to expose the textured implant.

FIGS. 1 and 2 illustrate a prosthetic hip stem implant 10 carrying a mask 12. As illustrated, mask 12 includes a plurality of openings 14 which define a predetermined pattern. The implant and mask of FIG. 1 are representative of blocks 50, 52 and 54 of FIG. 5.

FIGS. 3 and 4 illustrate the implant 10 of FIG. 1 after media blasting and with the mask removed. The implant of FIGS. 3 and 4 are representative of block 58 of FIG. 3.

The blasting media may be but should not be limited to the following known media in the form of bead, grit or particle, aluminum oxide, zirconium oxide, silicon dioxide (glass), cobalt-chrome molybdnemum alloy, stainless steel, cast iron or chilled iron, plain carbon steel, titanium, titanium alloys, magnesium oxides or other ceramics.

The mask is preferably resilient in nature and may be formed from any of the following materials: rubber, vinyl, metal, polymers, ceramic, or composite materials. This list should not be considered limiting or exclusive.

It may prove advantageous to form the mask from a shrinkable material to make the formation of the pattern easier and to make it easier to place the mask on the implant. After use, the shrinkable mask would be discarded.

During the blasting step of block 56, blasting media which contact the mask would be bounced off from the implant, or erroding the masking material without damaging the implant, while blasting media passing through openings 14 of mask 12 would contact the outer surface of the implant 10 eroding the surface a small amount. Eventually, enough particles will contact the implant through the opening of the mask to fully erode or change the surface of the implant exposed. The duration of the blasting step will be dependant upon many known factors within the media blasting art such as; the hardness of the implant material, the hardness of the media, the pressure at which the media is directed toward the implant. Blasting can be done manually or with an automated machine. It can also be done dry or wet. In dry blasting, air or a suitable fluid is used to carry the media. In wet blasting, water or a suitable liquid is used to carry the blasting material. Once blasting is completed and the mask is removed, portions of the implant covered by the mask will be unaffected while portions exposed will be textured. FIG. 3 illustrates a textured pattern resulting from blasting under the method of the invention with the mask illustrated in FIG. 1. FIG. 4 illustrates an enlarged cross section of an area 15 textured in accordance with the method of the invention.

While the invention has been described and illustrated for providing a textured surface on a hip stem implant to promote the mechanical interlock between a bone cement and the implant, such should not be considered a limitation on the method of the invention. The method has a wide variety of applications such as providing a textured surface for bony ingrowth, for bonding bioactive ceramics such as hydroxyapatite and tricalcium phosphate to the surface of an implant; texturing polymers for a better bond; or to increase the surface friction on external orthopaedic fixation devices, to name a few examples.

It should, therefore, be understood that the invention is not to be limited to the precise method described but may be modified within the scope of the appended claims.

I claim:

1. A method of providing a textured outer surface on an orthopaedic implant, the method comprising the steps of:
   a) providing an orthopaedic implant having an outer surface;
   b) providing a mask having a plurality of openings formed therein in a predetermined pattern;
   c) placing said mask on said implant such that portions of the outer surface of said implant are exposed by said openings in said mask, applying heat to the mask sufficient to cause said mask to shrink into a tight fit with said implant;
   d) subjecting said implant with said mask placed thereon to blasting by an erosive media, wherein media contacting the mask is prevented from contact with the implant and media passing through said openings in the mask contacting said portions of the implant; and
   e) removing said mask from said implant.

2. The method of claim 1 wherein step b includes the steps of:
   a) providing a material which will be generally reflective of the erosive media;
   b) forming a predetermined pattern of openings in said material; and
   c) forming said material into a shape generally conforming to the shape of said implant.

* * * * *